United States Patent
Freidberg

(10) Patent No.: US 7,108,717 B2
(45) Date of Patent: *Sep. 19, 2006

(54) STENT COVERED WITH HETEROLOGOUS TISSUE

(75) Inventor: Carlos Vonderwalde Freidberg, Roma Sur (MX)

(73) Assignee: Design & Performance - Cyprus Limited, Nicosia (CY)

(*) Notice: Subject to any disclaimer, the term of this patent is extended or adjusted under 35 U.S.C. 154(b) by 0 days.

This patent is subject to a terminal disclaimer.

(21) Appl. No.: 10/138,587

(22) Filed: May 3, 2002

(65) Prior Publication Data

US 2002/0151969 A1 Oct. 17, 2002

Related U.S. Application Data

(63) Continuation of application No. 08/935,784, filed on Sep. 23, 1997, now Pat. No. 6,468,300.

(51) Int. Cl.
*A61F 2/06* (2006.01)

(52) U.S. Cl. .................. 623/1.41; 623/1.13; 623/23.72

(58) Field of Classification Search .............. 606/194, 606/195, 153; 623/1.13, 1.23, 2.14, 903, 623/23.72, 1.41, 1.47
See application file for complete search history.

(56) References Cited

U.S. PATENT DOCUMENTS

| | | | | | |
|---|---|---|---|---|---|
| 4,400,833 | A | * | 8/1983 | Kurland | 3/1 |
| 4,470,157 | A | * | 9/1984 | Love | 623/2 |
| 4,477,930 | A | * | 10/1984 | Totten et al. | 623/2 |
| 4,502,159 | A | | 3/1985 | Woodroof et al. | 3/1.4 |
| 5,383,928 | A | * | 1/1995 | Scott et al. | 623/1 |
| 5,489,298 | A | * | 2/1996 | Love et al. | 623/2 |
| 5,512,291 | A | * | 4/1996 | Li | 424/443 |
| 5,549,663 | A | * | 8/1996 | Cottone, Jr. | 623/1 |
| 5,556,414 | A | | 9/1996 | Turi | 606/198 |
| 5,571,173 | A | * | 11/1996 | Parodi | 623/1 |
| 5,575,818 | A | | 11/1996 | Pinchuk | 623/1 |
| 5,584,876 | A | | 12/1996 | Bruchman et al. | 623/1 |
| 5,599,307 | A | | 2/1997 | Bacher et al. | 604/101 |
| 5,628,786 | A | | 5/1997 | Banas et al. | 623/1 |
| 5,641,373 | A | | 6/1997 | Shannon et al. | 156/242 |
| 5,653,743 | A | | 8/1997 | Martin | 623/1 |
| 5,653,747 | A | | 8/1997 | Dereume | 623/1 |
| 5,667,523 | A | | 9/1997 | Bynon et al. | 606/198 |
| 5,674,298 | A | * | 10/1997 | Levy et al. | 8/94.11 |
| 5,693,085 | A | | 12/1997 | Buirge et al. | 623/1 |
| 5,707,385 | A | * | 1/1998 | Williams | 606/192 |
| 5,723,004 | A | | 3/1998 | Dereume et al. | 623/1 |
| 5,782,914 | A | * | 7/1998 | Schankereli | 623/11 |
| 5,865,723 | A | * | 2/1999 | Love | 623/1 |

FOREIGN PATENT DOCUMENTS

| | | |
|---|---|---|
| EP | 0 839 506 A1 | 10/1997 |
| WO | WO 93/20757 | 10/1993 |
| WO | WO 94/15583 | 7/1994 |
| WO | WO 97/09006 | 3/1997 |
| WO | WO 97/12563 | 4/1997 |
| WO | WO 97/24081 | 10/1997 |

* cited by examiner

Primary Examiner—Paul Prebilic

(57) ABSTRACT

A covered stent assembly comprising a tubular, expandable stent having a metallic framework covered with a cylinder of biocompatible, non-thrombogenic expandable material, such as heterologous tissue. In a preferred embodiment, the metallic framework is positioned coaxially within a cylinder of bovine pericardial tissue. A catheter may be used to deliver the stent assembly to a desired region in the lumen of a patient. The metallic framework is then expanded to seat the assembly within the lumen.

6 Claims, 1 Drawing Sheet

STENT COVERED WITH HETEROLOGOUS TISSUE

RELATED APPLICATION

This application is a continuation of application Ser. No. 08/935,784, filed Sep. 23, 1997, now U.S. Pat. No. 6,468,300, which is incorporated herein in its entirety.

FIELD OF THE INVENTION

This invention relates to the field of expandable intraluminal support devices and more particularly to stents covered with heterologous tissue.

BACKGROUND OF THE INVENTION

Typically, stents are expandable, tubular metallic devices that are positioned within a patient's vasculature or other body lumen and expanded in order to support a vessel or body lumen and allow the flow of blood or other body fluids. Often, the stents are formed from a deformable metal and delivered using a balloon-type catheter. By advancing the catheter through the body lumen, the stent may be delivered to a desired position. Inflating the balloon then deforms the stent into an expanded configuration, seating it within the artery or other body lumen. Other implementations make use of a self-expanding stent formed from a psuedoelastic material that is delivered n a constricted condition and when released spontaneously expands to an enlarged configuration. In other embodiments, a stent made of shape memory alloy (NiTi) is inserted into the body lumen in a martensitic phase and transforms to austenite which has an expanded memory when raised to a temperature above the transformation temperature, usually less than 45° C.

Stents are often used in conjunction with an intravascular treatment for obstructive coronary artery disease. For example, ablation, atherectomy, balloon large percentage of percutaneous transluminal coronary angioplasty (PTCA) patients and rates can be even higher with other procedures. The prior art has employed a number of mechanical and pharmacological strategies to reduce the restenosis rate, but none have been particularly effective. Accordingly, stents have been proposed to maintain the patency of a treated vessel and prevent restenosis. Using stents, restenosis rates have fallen to less than 20%.

Restenosis is thought to be a natural healing reaction provoked by injury from the intravascular procedure. The healing process frequently causes thrombosis and may lead to intimal hyperplasia that occludes the vessel. Although helpful in reducing restenosis, stents do not represent a complete solution. The framework of the stent may still allow migration and proliferation of the smooth muscle cells, while the stent itself can be thrombogenic. To address these problems, stents have been covered with DACRON, PTFE and autologous vein and the surface has seeded with endothelial cells or otherwise treated. Each of these solutions suffer from certain drawbacks, such as not being biocompatible, lacking sufficient mechanical strength, having a surface that is difficult to prepare, lack of ready availability and being thrombogenic.

Thus, there remains a need for a stent capable of minimizing restenosis while having a consistency similar to the native artery, a non-thrombogenic surface and sufficient mechanical strength as well as being biocompatible and readily available. This invention satisfies these and other needs.

SUMMARY OF THE INVENTION

The invention is a stent assembly suitable for maintaining the patency of a bodily lumen, generally comprising an expandable, tubular framework comprising a stent at least in part within a cylinder of biocompatible, non-thrombogenic expandable material such as heterologous tissue. Preferably, the heterologous tissue comprises bovine pericardium, but other preferred embodiments include porcine pericardium, aortic leaflet and other suitable heterologous tissue. The expandable, tubular framework may be a conventional metallic stent.

This invention is also directed to a method for maintaining the patency of a bodily lumen comprising the steps of mounting a stent assembly of a tubular expandable, metallic framework forming the stent coaxially disposed within a cylinder of biocompatible, non-thrombogenic expandable material such as heterologous tissue on an expandable member on the distal extremity of a catheter; advancing the catheter through the bodily lumen until the stent assembly is positioned at a desired location; expanding the stent assembly by expanding the expandable member onto which the stent assembly is mounted to anchor it within the bodily lumen; contracting the expandable member, e.g. deflating the balloon, and withdrawing the catheter. The expanded cylinder of biocompatible, non-thrombogenic expandable material such as heterologous tissue should extend over a substantial portion, preferably all, of the stenotic region in which it is disposed.

DETAILED DESCRIPTION OF THE INVENTION

Figure 1:
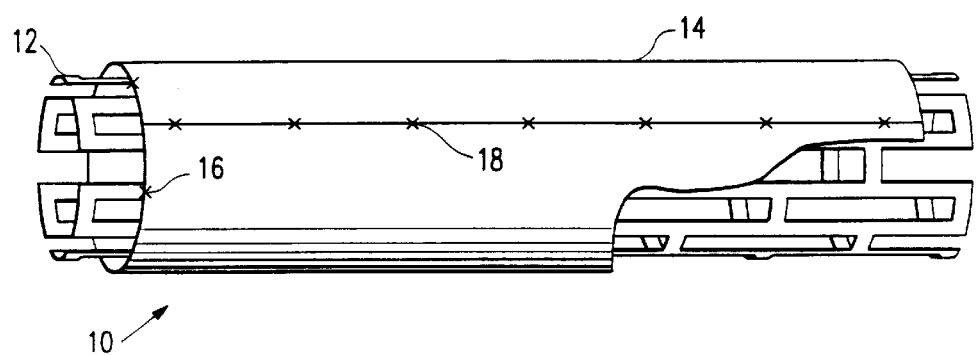
FIG. 1 is an isometric view, partially in section, of a stent of the invention showing the tubular, expandable, metallic framework positioned coaxially within a cylinder of heterologous tissue.

As shown in FIG. 1, a stent assembly 10 of this invention generally comprises a tubular, expandable metallic framework forming the stent 12 positioned coaxially within a cylinder 14 of heterologous tissue. Preferably, metallic stent 12 extends about 1 mm beyond each end of cylinder 14 to prevent prolapse of the tissue into the lumen of the stent when it is expanded. Cylinder 14 may be secured to metallic framework 12 by any suitable means. For example, four radially spaced sutures 16 may be placed at each end of cylinder 14.

Cylinder 14 preferably comprises bovine pericardium, a material shown to resist suture line bleeding, require no pre-clotting, support endothelialization and have an excellent host-tissue response. Further, bovine pericardial tissue has an elasticity of up to about 30% which allows the tissue cylinder to conform to both the unexpanded and expanded configurations of the metallic framework without adding a great deal of bulk which increases the profile on the balloon. Other heterologous tissue suitable in the practice of the invention includes porcine pericardium, aortic leaflet and others.

Useful heterologous tissue is relatively impenetrable, which prevents tissue build up and the migration of smooth muscle cells through the stent framework. A particularly preferred bovine pericardium has cross-linked collagen and is available from Bio Vascular. Bovine pericardium tissue is available in a thickness ranging from about 0.25 mm to about 0.75 mm, with an average of about 0.45 mm. Thicknesses of 0.45 mm and less are preferred, so long as the mechanical strength remains sufficient.

Metallic stent 12 may comprise any suitable conventional stent. For example, Micro Stent II, available from Arterial Vascular Engineering, and Multi-Link, available from Guidant, have proven useful. Other stents that may be used in the practice of this invention include the Palmaz-Shatz stent from Johnson and Johnson, the Gianturco stent from Cook Incorporated and other commercially available stents. Conventional balloon expandable stents are preferred, but, as previously mentioned, self-expanding stents formed from shape memory materials are also suitable.

The cylinder of heterologous tissue 14, may be formed by cutting a rectangle of tissue having a length about 2 mm shorter than the stent on which it is to be mounted and a width about equal to the circumference of the expanded stent. The two sides corresponding to the length of the stent then may be secured together, such as by sewing with 6-0 or 7-0 polypropylene sutures. Other means for securing the sides of the stent cover together include mechanical means such as staples, adhesive or chemical bonding and the like. It may be desirable to support the tissue while manipulating it. For example, a 9 French introducer dilator may be used to support a 3 mm diameter cylinder, an 11 French dilator for a 3.5 mm cylinder and a 12 French dilator for a 4 mm cylinder. The tissue should be kept wet at all times during manipulation. Additionally, radio-opaque markers, such as rings of gold or platinum, may be added to the outer layer of the tissue so that the integrity of the cylinder may be assured before deployment. The cylinder of heterologous tissue is configured to be mounted onto a stent and generally has a length of about 5 to about 80 mm, preferably about 10 to about 50 mm and a diameter of about 2 to about 6 mm preferably about 2.5 to about 5 mm.

The use of the covered stent system generally follows conventional procedures. In particular, a guidewire is back-loaded into a delivery catheter having the covered stent assembly 10 loaded over an inflatable balloon or on a self expanding stent delivery system. The catheter and guidewire are percutaneously introduced by means of a conventional Seldinger technique and a 9 or 10 French guiding catheter into the patient's arterial system. The guidewire is advanced out delivery catheter through the vasculature under fluoroscopic imaging until it crosses a stenotic region. Then the catheter is advanced over the guidewire until the stent 10 is positioned at the desired location within the stenotic region. Then, the balloon is inflated or the securing mechanism of the self expanding stent is released to expand metallic framework 12 and tissue cylinder 14, seating the assembly within the vessel. The balloon is then deflated and the catheter is removed, leaving the expanded stent assembly in place.

Although primarily described with respect to preventing restenosis in angioplasty patients, the covered stents of this invention may be used in a number of coronary artery, peripheral artery and non-vascular applications. For example, coronary artery applications include use in ectatic arteries and ectatic arteries containing an obstructive lesion, aneurismatic arteries, saphenous vein grafts and native arteries. Peripheral artery applications include aortic abdominal aneurysm and other aneurismatic peripheral arteries, transjugular intrahepatic portal shunt, percutaneous transluminal angioplasty, fistula closing and neuro interventions (such as aneurysms and arterial-venous malformations). Finally, the covered stents of this invention may be used in urological, gastroenterological, respiratory and other non-vascular applications.

A general description of the device of the present invention as well as a preferred embodiment of the present invention has been set forth above. One skilled in the art will recognize and be able to practice many changes in many aspects of the device described above, including variations that fall within the teachings of this invention. The spirit and scope of the invention should be limited only as set forth in the claims which follow.

What is claimed is:

1. A cylinder of heterologous tissue which is configured to fit over an intraluminal stent, which has a first end with a diameter and a second end with a diameter equal to the diameter of the first end, which is formed of a single layer of heterologous tissue having first and second opposed edges oriented along the longitudinal axis of the cylinder and having a thickness of less than about 0.45 millimeters, which has a seam oriented along the longitudinal axis of the cylinder and formed by the first edge with a first edge facing and the second edge with a second edge facing secured to the first edge at a plurality of intermediate locations along the seam from the first end to the second end to form the cylinder, the second edge facing abutting the first edge facing at the seam.

2. The cylinder of claim 1 having a length of about 5 to about 80 mm.

3. The cylinder of claim 1 having a length of about 10 to about 50 mm.

4. The cylinder of claim 1 having a diameter of about 2 to about 6 mm.

5. The cylinder of claim 1 having a diameter of about 2.5 to about 5 mm.

6. The cylinder of claim 1 wherein the heterologous tissue of the single tissue layer is selected from the group consisting of bovine pericardium, porcine pericardium, and aortic leaflet.

* * * * *